US 6,410,320 B1

(12) United States Patent
Humes

(10) Patent No.: US 6,410,320 B1
(45) Date of Patent: Jun. 25, 2002

(54) METHOD AND COMPOSITIONS FOR ISOLATION AND GROWTH OF KIDNEY TUBULE STEM CELLS, IN VITRO KIDNEY TUBULOGENESIS AND EX VIVO CONSTRUCTION OF RENAL TUBULES

(75) Inventor: H. David Humes, Ann Arbor, MI (US)

(73) Assignee: The University of Michigan, Ann Arbor, MI (US)

( * ) Notice: Subject to any disclaimer, the term of this patent is extended or adjusted under 35 U.S.C. 154(b) by 0 days.

(21) Appl. No.: 09/494,044

(22) Filed: Jan. 31, 2000

Related U.S. Application Data

(63) Continuation-in-part of application No. 07/844,758, filed on Mar. 2, 1992, now Pat. No. 5,429,938.

(51) Int. Cl.[7] .............................. C12N 5/00; C12N 5/02; C12N 5/06; C12N 5/08; C12N 5/10; C12N 15/63; C12N 15/85; A61K 7/035; A01W 63/00

(52) U.S. Cl. ........................ 435/369; 435/363; 435/455; 435/325; 424/69.1; 424/93.1; 424/93.2; 424/93.21

(58) Field of Search ................................. 435/325, 69.1, 435/455, 363, 369; 424/93.21, 93.1, 93.2

(56) References Cited

U.S. PATENT DOCUMENTS

| 3,734,851 A | 5/1973 | Matsumura |
| 4,242,460 A | 12/1980 | Chick et al. |
| 4,354,933 A | 10/1982 | Lester |
| 5,360,790 A | 11/1994 | Humes |
| 5,429,938 A | 7/1995 | Humes |
| 5,516,680 A | 5/1996 | Naughton et al. |
| 5,549,674 A | 8/1996 | Humes et al. |
| 5,686,289 A | 11/1997 | Humes et al. |
| 5,733,727 A | 3/1998 | Field |
| 5,833,978 A | 11/1998 | Tremblay |
| 5,906,817 A | 5/1999 | Moullier et al. |
| 5,919,449 A | 7/1999 | Dinsmore |
| 6,060,270 A | 5/2000 | Humes |
| 6,150,164 A | 11/2000 | Humes |

FOREIGN PATENT DOCUMENTS

| GB | 1 479 002 | 6/1974 |
| WO | WO 89/01967 | 3/1989 |
| WO | WO 91/00119 | 1/1991 |
| WO | WO 92/07615 | 5/1992 |
| WO | WO 93/17696 | 9/1993 |

OTHER PUBLICATIONS

HD Humes et al., Laboratory Investigation. "Effects of Transforming Growth Factor–Beta, Transforming Growth Factor–alpa, and Other Growth Factors on Renal Proximal Tubule Cells," 1991, vol. 64, No. 4, pp. 538–545.*
FM Watt et al., Stem Cell Research and Ethics, "Out of Eden: Stem Cells and Their Niches," Review, Feb. 2000, vol. 287, pp. 1427–1430.*
R. Montesano et al., Cell, "Induction of Epithelial Tubular Morphogenesis in Vitro by Fibroblast–Derived Soluble Factors," Aug. 1991, vol. 66, pp. 697–711.*
Q Al–Awqati, Current Opinion in Nephrology and Hypertension,"Cellular and molecular mechanisms of renal development and tubulogenesis," Oct. 1992, 1:53–58.*
SH Orkin et al., Report and Recommendations of the Panel to Assess the NIH Investment in Research on Gene Therapy, Dec. 1995, pp. 1–41.*

(List continued on next page.)

Primary Examiner—James Ketter
Assistant Examiner—Janice Li
(74) Attorney, Agent, or Firm—Oblon, Spivak, McClelland, Maier & Neustadt, P.C.

(57) ABSTRACT

Methods, including culture media conditions, which provide for isolation and purification of renal tubule stem cells and for in vitro kidney tubulogenesis are disclosed. The methods rely on culturing adult kidney cells in a culture media treated with combinations of transforming growth factor-$\beta_1$, epidermal growth factor, and all-trans retinoic acid.

3 Claims, 7 Drawing Sheets

OTHER PUBLICATIONS

H. David Humes et al., Replacement of Renal Function in Uremic Animals with a Tissue–Engineered Kidney, *Nature Biotechnology*, vol. 17, pp. 451–455, May 1999.

Roger C. Bone Systemic Inflammatory Response Syndrome: A Unifying Concept of Systemic Inflammation, *Sepsis and Multiorgan Failure*, 1997, pp. 3–10.

H. David Humes et al., Tissue Engineering of a Bioartificial Renal Tubule Assist Device: In Vitro Transport and Metabolic Characteristics, *Kidney International*, vol. 55 (1999), pp. 2502–2514.

H. David Humes, Bioartificial Kidney for Full Renal Replacement Therapy, *Seminars in Nephrology*, vol. 20, No. 1, Jan. 2000, pp. 71–82.

John M. Walker et al., *The Language of Biotechnology*, 1988, p. 126.

R. Ian Freshney, *Culture of Animal Cells, A Manual of Basic Technique*, Second Edition, 1987, pp. 1–13, and pp. 197–206.

Sherrill M. MacKay et al., Tissue Engineering of a Bioartificial Renal Tubule, *ASA/O Journal*, vol. 44, No. 3, May–Jun. 1998, pp. 179–183.

Sally Pobojewski, U Researchers Unveil Component of Bio–Artificial Kidney, *The University Record*, May 24, 1999.

Charles Natanson et al., Role of Endotoxemia in Cardiovascular Dynsfunction and Mortality, *The Journal of Clinical Investigation, Inc.*, vol. 83, Jan. 1989, pp. 243–251.

Bradley D. Freeman et al., Continuous Arteriovenous Hemofiltration Does Not Improve Survival in a Canine Model of Septic Shock, *Journal of the American College of Surgeons*, Mar. 1995, vol. 180, pp. 286–291.

J. A. Kellum, Immunomodulation in Sepsis: The Role of Hemofiltration, *Minerva Anestesiologica*, vol. 65, No. 6, pp. 410–418.

Gordon R. Bernard, M.D. et al., Efficacy and Safety of Recombinant Human Activated Protein C for Severe Sepsis: *The New England Journal of Medicine*, vol. 344, No. 10, Mar. 8, 2001, pp. 699–709.

Diep D. Tran et al., Age, Chronic Disease, Sepsis, Organ System Failure, and Mortality in a Medical Intensive Care Unit, *Critical Care Medicine*, vol. 18, No. 5, pp. 474–479, May 1990.

S. C. Donnelly et al., Mediators, Mechanisms and Mortality in Major Trauma, *Resuscitation*, vol. 28, pp. 87–92, 1994.

Roger C. Bone, M.D. et al., A Controlled Clinical Trial of High–Dose Methylprednisolone in the Treatment of Severe Sepsis and Septic Shock, *The New England Journal of Medicine*, vol. 317, No. 11, pp. 653–658.

K. D. Horn, Evolving Strategies in the Treatment of Sepsis and Systemic Inflammatory Response Syndrome (SIRS), *Q. J. Med*, 1998, vol. 91, pp. 265–277.

Michael R. Pinsky, Serum Cytokine Levels in Human Septic Shock, *Chest*, vol. 103, No. 2, Feb. 1993, pp. 565–575.

Claire Marty et al., Circulating Interleukin–8 Concentrations in Patients with Multiple Organ Failure of Septic and Nonseptic Origin, *Critical Care Medicine*, vol. 22, No. 4, pp. 673–679, Apr. 1994.

Pierre Damas, M.D., Ph.D. et al., Tumor Necrosis Factor and Interleukin–1 Serum Levels During Severe Sepsis in Humans, *Critical Care Medicine*, vol. 17, No. 10, pp. 975–978, Oct. 1989.

Charles A. Dinarello, The Proinflammatory Cytokines Interleukin–1 and Tumor Necrosis Factor and Treatment of the Septic Shock Syndrome, *The Journal of Infectious Diseases*, 1991: 163, pp. 1177–1184.

Thierry Calandra et al., Prognostic Values of Tumor Necrosis Factor/Cachectin, Interleukin–1, Interferon–α, and Interferon–γ in the Serum of Patients with Septic Shock, *The Journal of Infectious Diseases*, 1990: 161, pp. 982–987.

J. X. Jiang et al., Plasma Cytokines and Endotoxin Levels in Patients with Severe Injury and Their Relationship With Organ Damage, *Injury*, vol. 28, No. 8, pp. 509–513, 1997.

Dorothy Breen et al., Acute Renal Failure as a Part of Multiple Organ Failure: The Slippery Slope of Critical Illness, *Kidney International*, vol. 53, Suppl. 66 (1998), pp. S–25–S33.

Mark J. Samak et al., Mortality Caused by Sepsis in Patients with End–Stage Renal Disease Compared with the General Population, *Kidney International*, vol. 58 (2000), pp. 1758–1764.

Mathias Girndt et al., Production in Interleukin–6, Tumor Necrosis Factor α and Interleukin–10 in vitro Correlates with the Clinical Immune Defect in Chronic Hemodialysis Patients, *Kidney International*, vol. 47 (1995), pp. 559–565.

Mathias Girndt et al., Impaired Cellular Immune Function in Patients with End–Stage Renal Failure, *Nephrol Dial Transplant*, (1999) 14: 2807–2810.

Melissa K. Thomas, M.D., Ph.D. et al., Hyptovitaminosis D in Medical Inpatients, *The New England Journal of Medicine*, vol. 338, No. 12, Mar. 19, 1998, pp. 777–783.

Roger C. Bone, M.D., Why Sepsis Trials Fail, *JAMA*, Aug. 21, 1996, vol. 276, No. 7, pp. 565–566.

Roger C. Bone, M.D., Toward a Theory Regarding the Pathogenesis of the Systemic Inflammatory Response Syndrome: What we Do and Do Not Know about Cytokine Regulation, *Crit Care Med*, 1996, vol. 24, No. 1, pp. 163–172.

C. Erik Hack et al., Interleukin–8 in Sepsis: Relation to Shock and Inflammatory Mediators, *Infection and Immunity*, Jul. 1992, vol. 60, No. 7, p. 2835–2842.

Roger C. Bone, M.D., Immunologic Dissonance: A Continuing Evolution in Our Understanding of the Systemic Inflammatory Response Syndrome (SIRS) And the Multiple Organ Dysfunction Syndrome (MODS): *Ann Intern Med.*, 1996, vol. 125, p. 680–687.

Roger C. Bone, M.D., Sepsis: A New Hypothesis for Pathogenesis of the Disease Process, *Chest*, vol. 112, No. 1, Jul. 1997, pp. 235–243.

John H. Reeves et al., Continuous Plasmafiltration in Sepsis Syndrome, *Crit Care Med*, 1999, vol. 27, No. 10, pp. 2096–2104.

An S. De Vriese et al., Cintinuous Renal Replacement Therapies in Sepsis: Where are the Data?, *Nephrol Dial Transplant*, (1998), vol. 13, pp. 1362–1364.

Jean–Louis Vincent, M.D. et al., Phase II Multicenter Clinical Study of the Platelet–Activating Factor Receptor Antagonist BB–882 in the Treatment of Sepsis, *Crit Care Med*, vol. 28, No. 3, 2000, pp. 638–642.

Quezado, et al., New Strategies for Combatting Sepsis: The Magic Bullets Missed the Mark . . . But the Search Continues, *Tibtech*, Feb. 1995, vol. 13, pp. 56–63.

John W. Christman, M.D., Strategies for Blocking the Systemic Effects of Cytokines in the Sepsis Syndrome, *Critical Care Medicine*, vol. 23, No. 5, pp. 955–963, 1995.

M. L. Kielar et al., The Liver Regulates Renal Ischemic Injury: A Possible Role for Renal IL6 and Hepatic IL10?, *Abstract*.

Kevin P. Lally et al., The Role of Anti–Tumor Necrosis Factor–α and Interleukin–10 in Protecting Murine Neonates from *Escherichia coli*, Sepsis, *Journal of Pediatric Surgery*, vol. 35, No. 6, Jun. 2000, pp. 852–855.

Keith R. Walley et al., Balance of Inflammatory Cytokines Related to Severity and Mortality of Murine Sepsis, *Infection and Immunity*, No. 1996, pp. 4733–4738, vol. 64, No. 11.

Tetsuya Matsumoto et al., Effect of Interleukin–10 on Gut–Derived Sepsis Caused by *Pseudomonas Aeruginosa* in Mice, *Antimicrobial Agents and Chemotherapy*, Nov. 1998, vol. 42, No. 11, p. 2853–2857.

Arnaud Marchant et al., Interleukin–10 Controsl Interferon–γ and Tumor Necrosis Factor Production During Experimental Endotoxemia, *Eur. J. Immunol.*, 1994, vol. 24, pp. 1167–1171.

Sherril M. MacKay et al., Tissue Engineering of a Bioartificial Renal Tubule, *ASAIO Journal*, 1998, pp. 179–183.

Ziad A. Massy, Reversal of Hyperhomocyst(e) Inaamia in Chronic Renal Failure—Is Folic or Foliniic Acid the Answer?, *Nephrol Dial Transplant*, (1999), vol. 14, pp. 2810–2812.

Raymond Vanholder et al., p–Cresol: A Toxin ρ–Cresol: A Toxin Revealing Many Neglected But Relevant Aspects of Uraemic Toxicity, *Nephol Dial Transplant* (1999) vol. 14, pp. 2813–2815.

Jürgen Bommer, Saving Erythropoietin by Administering L–Carnitine?, *Nephrol Dial Transplant*, (1999), vol. 14, pp. 2819–2821.

Max Dratwa, Pre–Emptive (CAPD—What Are the Arguments?, *Nephrol Dial Transplant*, (1999), vol. 14, pp. 2822–2823.

Bart D. Maes et al., Anti–Interleukin–2 Receptor Monoclonal Antibodies in Renal Transplantation, *Nephrol Dial Transplant*, (1999) vol. 14, pp. 2824–2826.

Andras Mogyorosi et al., GLUT1 and TGF–β: The Link Between Hyperglycaemia and Diabetic Nephropathy, *Nephrol Dial Transplant*, (1999), vol. 14, pp. 2827–2829.

Tze Kin Ip et al., Renal Epithelial–Cell–Controlled Solute Transport Across Permeable Membranes as the Foundation for a Bioartificial Kidney, *Artificial Organs*, vol. 13, No. 1, pp. 58–65, 1989.

Elliot L. Chaikof, Engineering and Material Considerations in Islet Cell Transplantation, *Ann. Rev. Biomed. Eng.*, 01: 103–127, 1999.

Abbie M. Jensen, et al., Expression of Sonic hedgehog and Its Putative Role as a Putative Role as a Precursor Cell Mitogen in the Developing Mouse Retina, *Development*, 124, 363–371, 1997.

Mark J. Horney et al., Elevated Glucose Increases Mesangial Cell Sensitivity to Insulin–Like Growth Factor I, *The American Physiological Society*, pp. F1045–F1053, 1998.

Barry M. Brenner, M.D., et al., Mechanics of Glomerular Ultrafiltration, *The New England Journal of Medicine*, vol. 297, 1977, pp. 148–154.

James A. Zwiebel, et al., High–Level Recombinant Gene Expression in Rabbit Endothelial Cells Transduced by Retroviral Vectors, *Science*, vol. 243, pp. 220–222.

David A. Dichek, M.D., et al., Seeding of Intravascular Stents With Genetically Engineered Endothelial Cells, *Circulation*, vol. 80, No. 5, Nov. 1989, pp. 1347–1353.

Barry M. Brenner, M.D., et al., Molecular Basis of Proteinuria of Glomerular Origin, *The New England Journal of Medicine*, Apr. 13, 1978, vol. 298, No. 15, pp. 826–833.

Lonnie D. Shea, et al., DNA Delivery From Polymer Matrices for Tissue Engineering, *Nature Biotechnology*, vol. 17, Jun. 1999, pp. 551–554.

Mickey C.–T. Hu, et al., FGF–18, a Novel Member of the Fibroblast Growth Factor Family, Stimulates Hepatic and Intestinal Proliferation, *Molecular and Cellular Biology*, Oct. 1998, pp. 6063–6074, vol. 18, No. 10.

Judah Folkman, et al., Angiogenesis, *The Journal of Biological Chemistry*, vol. 267, No. 16, Jun. 1992, pp. 10931–10934.

Joseph A. Madri, et al., Phenotypic Modulation of Endothelial Cells by Transforming Growth Factor–β Depends Upon the Composition and Organization of the Extracellular Matrix, *The Journal of Cell Biology*, vol 106, Apr. 1988, 1375–1384.

Yukio Tsurumi, M.D., et al., Direct Intramuscular Gene Transfer of Naked DNA Encoding Vascular Endothelial Growth Factor Augments Collaterla Development and Tissue Perfusion, *Circulation*, vol. 94, No. 12, Dec. 15, 1996, pp. 3281–3290.

Shailen R. Patel, et al., Safety of Direct Myocardial Administration of an Adenovirus Vector Encoding Vascular Endothelial Growth Factor 121, *Human Gene Therapy*, vol. 10, 1331–1348, May 20, 1999.

John A. Thompson, et al., Site–Directed Neovessel Formation in Vivo, *Reports*, vol. 241, Sep. 9, 1988, pp. 1349–1352.

James M. Wilson, et al., Implantation of Vascular Grafts Lined with Genetically Modified Endothelial Cells, *Science*, vol. 244, pp. 1344–1346, Jun. 16, 1989.

H. David Humes, et al., Interaction Between Growth Factors and Retinoic Acid in the Induction of Kidney Tubulogenesis in Tissue Culture, *Experimental Cell Research*, vol. 201, pp. 8–15, 1992.

H. David Humes et al., Tubulogenesis from Isolated Single Cells of Adult Mammalian Kidney: Clonal Analysis with a Recombinant Retrovirus, *Am. J. Physiol*, (Renal Fluid Electrolyte Physiol. 40) 271, F42–F49, 1996.

J. M.W. Slack, From Egg to Embryo, Regional Specification in Early Development, Second Edition, Cambridge University Press, 1991 pp. 188–193.

T.S. Okada, Transdifferentation, *Flexibility in Cell Differentiation*, Clarendon Press, 1991, pp. 1–13 and 178–185.

Scott F. Gilbert, Early Vertebrate Development: Neurulation and Ectoderm, *Developmental Biology*, Sinauer Associates, 1991, pp. 188–191 and 229–237.

Taub et al., 1990, Proc. Nat. Acad. Sci. USA, 87: 4002–4006.

Potten et al., 1990, Development, 110: 1001–1020.

Parczyk et al., 1989, J. Biol. Chem., 264(28): 16837–16846.

Humes et al., 1992, Ep. Cell Res., 201:8–15.

Humes et al., 1991, Lab. Invest., 64(4):538–545.

Watson et al., 1987, in:Molecular Biology of the Gene, Fourth Edition, Benjamin/Cummings Publ. Co., Menlo Park CA, p. 313.

Robinson, 1993, TIBTECH, 11: 155.

Friedmann, 1993, TIBTECH, 11: 156–159.

Dillon, 1993, TIBTECH, 11: 167–173.

Brown, 1993, in: The Washington Post, Friday Dec. 8, 1995, pp. A1 and A22.

Stark et al., 1994, Nature 372: 679–683.

Herzlinger et al., 1994, Developmental Biology, 166: 815–818.

\* cited by examiner

METHOD AND COMPOSITIONS FOR ISOLATION AND GROWTH OF KIDNEY TUBULE STEM CELLS, IN VITRO KIDNEY TUBULOGENESIS AND EX VIVO CONSTRUCTION OF RENAL TUBULES

This application is a continuation-in-part of U.S. Ser. No. 07/844,758, filed on Mar. 2, 1992, now U.S. Pat. No. 5,429,938.

The subject matter of this application is based on research in part funded by the National Institutes of Health. The government may have certain rights in this application.

BACKGROUND OF THE INVENTION

1. Field of the Invention

This invention relates to methods and compositions for isolating, growing and transforming kidney tubule stem cells.

2. Discussion of the Background

Renal failure is a common clinical syndrome, defined as a decline in renal function, either acutely or chronically. The clinical manifestations of this disorder arise from a decline in glomerular filtration rate and an inability of the kidney to excrete the toxic metabolic wastes produced by the body. The complete treatment of this condition is dependent upon the replacement of filtrative, reabsorptive, homeostatic and endocrine functions of the kidney as an integrated organ structure.

In this regard, the function of a tissue is critically dependent upon the spatial arrangement of its constituent cells. The precise molecular determinants of such pattern formation both in vitro and in vivo is complicated, but soluble factors, such as growth factors, and insoluble factors, such as extracellular matrix molecules, most likely play fundamental roles in this process. Soluble molecules include both growth promoters (epidermal growth factor) and growth inhibitors (transforming growth factor-β). Insoluble factors include complex extracellular matrices (collagen gels, Matrigel) or extracellular matrix (ECM) molecules (laminin, fibronectin, collagen types I and IV).

This critical interplay of structure and function is demonstrated in the embryonic morphogenesis of the kidney, which is dependent upon a finely orchestrated interaction between mesenchyme and epithelium. The initial steps in differentiated nephrogenesis are followed by the development of tubule epithelial cell polarity and lumen formation. Coincident with the onset of cell polarity and tubulogenesis, as defined by both morphologic and directional transport properties, is the appearance of the A chain of laminin, a cell attachment protein of the basement membrane, in the basal regions of the mesenchymal cell aggregate. A sequential series of growth and further differentiation processes then follows to result eventually in a fully formed and functional kidney.

If this complex process of kidney organogenesis could be mimicked in vitro, novel methods for the treatment of renal failure could become available. Various tissue engineering products could be constructed from both semi-synthetic and organic components for complete replacement of renal function in patients with renal failure. Such advances might also allow the development of bioreactors comprising purely organic material for the substitution of renal function in a patient whose kidneys are compromised. These developments could also allow for kidney organogenesis, resulting in the growth of an organic kidney in vitro, from the isolation of renal tubule stem cells from a donor and subsequent growth and differentiation. The in vitro kidney could later be transplanted to the donor of the original renal cells, resulting in replacement of renal function without any fear of transplant rejection or immunosuppressive therapy. The availability of renal tubule stem cells could also promote an efficient process for incorporation of various genes into renal cells for gene therapy of various diseases.

However, such developments are predicated upon the development of a culture system which allows for isolation and growth of kidney tubule stem cells and for in vitro tubulogenesis.

Such a culture system has not-been achieved in the prior art, although in vivo kidney cells have demonstrated a potential for differentiation and regeneration. As demonstrated by Humes et al., *J. Clin. Invest.* 84:1757–61 (1989) and by Coimbra et al., *Am. J. Physiol.* 259:F438–F443 (1990), complete recovery of renal function can occur after severe nephrotoxic or ischemic acute renal injury that was of a magnitude to produce complete renal failure. Thus, some subset of renal proximal tubule cells apparently has the ability in vivo to regenerate and form a fully functional, differentiated epithelium. However, such results are doubtlessly the result of the complex interaction of a large number of biological factors responsible for growth, differentiation, pattern formation and morphogenesis of the renal tubule.

Certain of these factors have been identified and employed in renal cell cultures. TGF-$\beta_1$ has been recently shown to transform a monolayer of renal proximal tubule cells in primary culture into a three-dimensional adhesive aggregate of cells, see Humes et al, *Lab. Invest.* 64:538–545 (1991). EGF has been shown to be a potent growth promoter for renal epithelial cells, see Norman et al, *Am. J. Physiol.* 253:F299–F309 (1987). Retinoic acid has been reported to increase laminin synthesis in embryonic cell lines by promoting laminin gene transcription, see Dziadpk et al, *Devel. Biol.* 111:372–382 (1985); Vasios et al, *Proc. Natl. Acad. Sci. (USA)* 86:9099–9103 (1989); and Rogers et al, *J. Cell. Biol.* 110:1767–1777 (1990). However, these efforts of the prior art have all failed to evoke tubulogenesis in renal cell cultures. Such tubulogenesis is the first step towards in vitro kidney organogenesis.

SUMMARY OF THE INVENTION

Accordingly, it is an object of this invention to provide novel methods, including culture media conditions, for in vitro kidney tubulogenesis.

It is another object of the present invention to provide novel methods for isolating and growing kidney tubule stem cells.

It is another object of this invention to provide a novel, functioning ex vivo kidney tubule tissue system.

It is another object of this invention to provide novel methods, including culture media conditions, for culturing renal tubule stem cells so as to effect gene therapy upon said cells.

The present invention provides methods and composition which satisfy all of the above objects of this invention, and other objects, as will be apparent from the description of the invention given hereinbelow.

The present invention is based on the inventor's discovery of novel methods, including culture media conditions, which provide for isolation and growth of kidney tubule stem cells, for in vitro kidney tubulogenesis and for ex vivo construction of renal tubules. These methods rely on culturing renal proximal tubule cells in a hormonally-defined culture medium which is treated with combinations of transforming growth factor-$\beta_1$ (TGF-$\beta_1$), epidermal growth factor (EGF) and the retinoid, all-trans retinoic acid (RA), while maintaining the culture under physiologically acceptable conditions.

The inventor has discovered that the administration of TGF-$\beta_1$, EGF and all-trans retinoic acid transform a confluent monolayer of renal proximal tubule cells into three-dimensional cell aggregates containing lumens within the interior of the cell clusters. The lumens were bordered by tubule cells possessing a polarized epithelial cell phenotype with extensive microvilli formation and tight junctional complexes along the luminal border.

In one embodiment all three factors are used to isolate and grow kidney tubule stem cells and to induce this phenotypic transformation. In an alternate embodiment all-trans retinoic acid and EGF are employed to isolate and grow kidney tubule stem cells and to induce tubulogenesis. It is possible to substitute transforming growth factor-$\alpha$ for EGF. These results demonstrate that the growth factors, TGF-$\beta_1$ and EGF, and the retinoid, all-trans retinoic acid, promote tubulogenesis of adult renal proximal tubule cells in kidney cell culture.

DETAILED DESCRIPTION OF THE PREFERRED EMBODIMENTS

Figure 1A:
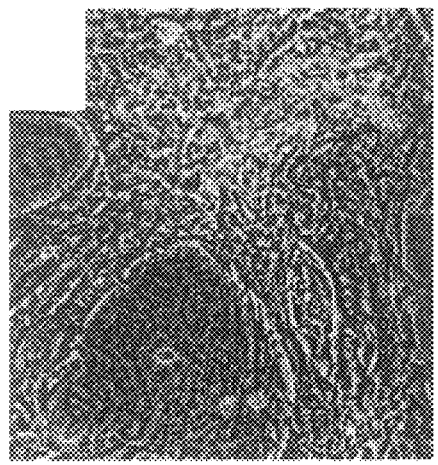
FIGS. 1a–1c is a photograph showing a representative phase contrast microscopy of renal proximal tubule cells plated into three-dimensional collagen gels after first, third, and fifth passage. (a) First Passage. Tubule cells formed monolayers on the surface of the collagen gel and no tubule-like aggregates were seen within the collagen (125×). (b) Third Passage. Tubule cells formed clusters of cells aggregating into circular tubule like structures (125×). (c) Fifth Passage. Tubule cells formed long branching tubule structures (125×).

The inventor has found that the treatment of a hormonally-defined renal cell culture with transforming growth factor-$\beta_1$, epidermal growth factor, and all-trans retinoic acid transformed a confluent monolayer of renal proximal tubule cells into epithelial cell aggregates containing lumens, bordered by cells with a differentiated polarized epithelial cell phenotype.

In a preferred embodiment of the present invention, transforming growth factor-$\beta_1$ is administered so as to achieve a concentration of from 0.1 ng/ml–1 mg/ml, epidermal growth factor in a concentration range of from 0.1 nM to 1 $\mu$M, and all-trans retinoic acid in a concentration range of from 0.01 $\mu$M to 100 $\mu$M.

Another, optional but important, embodiment of the present invention, resides in the addition of soluble factors to the renal tubule stem cell culture. In a particularly preferred aspect of this embodiment, these soluble factors include fetal calf serum, prostagladins, hydrocortisone trioodothyronine, selenium, fibroblastic growth factor, transforming growth factor-$\alpha$, hepatocyte growth factor, and combinations thereof.

These soluble factors are preferably added in the following concentrations: fetal calf serum, 3–25% (volume/volume) of growth media; prostaglandin $E_1$, 1 to 100 ng/ml; triiodothyronine, 0.1 nM to 1 $\mu$M; selenium, 0.001 to 1.00 $\mu$M; cholesterol, 1.0 nM to 0.10 $\mu$M; transferrin, 1 to 50 $\mu$g/ml; transforming growth factor-$\alpha$, 0.1 nM to 1 $\mu$M; insulin, 1-50 $\mu$g/ml; hydrocortisone, 1 nm to 1 $\mu$M; and hepatocyte growth factor 0.1 ng/ml to 100 ng/ml.

Another, optional but important, embodiment of the present invention, resides in the addition of insoluble factors to the renal tubular stem cell culture. These insoluble factors include a variety of extracellular matrix molecules. Included in these extracellular matrix molecules are Type I collagen, Type IV collagen, laminin, proteoglycans, fibronectin, and combinations thereof.

These insoluble factors are preferably added in the following concentrations: collagen, Type I, 1 to 5 mg/ml;

collagen, Type IV, 0.01 to 5 mg/ml; laminin, 10 to 1000 μg/ml; heparin sulfate, 10 to 1000 μg/ml; and heparin, 10 to 1000 μg/ml.

An additional preferred embodiment of the present invention resides in the addition of both soluble factors and insoluble factors to the renal tubule stem cell cultures.

In the present invention, the techniques used to obtain, collect and grow the renal cells and the culture systems in which the renal cells are grown are conventional ones and are described in Taub et al, *J. Biol. Chem.*, 254, 11440–11444; Taub et al, *J. Cell Physiol.*, 106 191–199; Taub et al, *J. Supramol. Struct*, 11, 207–216; Taub et al, *J. Cell Physiol*, 105, 369–378; Taub et al, *Proc. Nat. Accad. Sci. USA*, 76, 3338–3342; Taub et al, *Ann. New York Acad Sci.*, 372, 406–421; Taub et al, *J. Supramol. Struct.*, 15, 63–72; and Taub et al, *J. Cell Physiol*, 114, 153–161; which are incorporated herein by reference.

In the present specification, the terms treatment and treating refer to a process or means of exposing the cultured cells to the substance being administered. The specific method of treatment varies, depending on the properties of the substance, If added in aliquots, the flow of the aliquot being added may be by gravity, by pump, or by any other suitable means. The flow may be in any direction or multiplicity of directions, depending upon the configuration and packing of the culture. Preferably, the substance is added in a manner such that it contacts the cell mass. Most preferably, it is added to the culture in a manner mimicking in vivo perfusion, i.e., it is perfused through at least part of the cell mass and up to the whole cell mass.

The term tubulogenesis denotes the de novo construction of three-dimensional cell aggregates containing lumens within the interior of the cell clusters. Such lumens are bordered by tubule cells possessing a polarized epithelial cell phenotype with extensive microvilli formation and tight junctional complexes along the laminal border.

In one embodiment, the ex vivo renal tubule tissue system may be implanted in a patient in need thereof. The renal cells comprising such a tubule tissue system may be either transformed or non-transformed cells. The implantation may be achieved by conventional techniques, such as, by graft or insertion.

Moreover, the renal tubule stem cell cultures of the present invention may serve as an important target in gene therapy. Gene therapy is a rapidly growing field in medicine which is of inestimable clinical potential. It comprises the insertion of genes into cells for the purpose of medicinal therapy. Research in gene therapy has been on-going for several years and has been conducted in several types of cells in vitro and in animal studies, and has recently entered the first human clinical trial. Gene therapy has many potential uses in treating disease and has been reviewed extensively. See, e.g., Boggs, *Int. J. Cell Cloning* 8, 80 (1990), Kohn et al, *Cancer Invest.* 7, 179 (1989), Lehn, *Bone Marrow Transp.* 5, 287 (1990), and Verma, *Scientific Amer.* 68 (1990). Suitable genetic diseases and disorders that may be treated with the transformed renal tubule stem cells of the present invention are described in Ellis, *Inborn Errors of Metabolism*, Croom Helm London, 1980, and Galjaard, *Genetic Metabolic Diseases*, Elsevier, New York, 1980, which are incorporated herein by reference.

The renal tubule stem cell system is an ideal choice for gene therapy. However, up to the present time renal tubule stem cells have not been accessible. With the methods and compositions of the present invention, renal tubule stem cells are now readily available for gene therapy, can be maintained in culture for unlimited periods of time, and upon reimplantation, may replace kidney function.

The renal tubule stem cells can be transformed with one or more genes providing for desired traits. Methods for transforming mammalian cells are well known and there is an extensive literature of which only a few references have been previously given. The constructs man employ the naturally occurring transcriptional initiation regulatory region, comprising the promoter and, as appropriate the enhancer, or a different transcriptional initiation region may be involved, which may be inducible or constitutive.

A large number of transcriptional initiation regions are available which are inducible or constitutive, may be associated with a naturally occurring enhancer, or an enhancer may be provided, may be induced only in a particular cell type, or may be functional in a plurality or all cell types. The transcriptional initiation region may be derived from a virus, a naturally occurring gene, may be synthesized, or combinations thereof.

Promoters which are available and have found use include the chromosomal promoters, such as the mouse or human metallothionein-I or II promoters, actin promoter, etc., or viral promoters, such as SV40 early gene promoters, CMV promoter, adenovirus promoters, promoters associated with LTRs of retroviruses, etc. These promoters are available and may be readily inserted into appropriate vectors which comprise polylinkers for insertion of the transcriptional initiation region as well as the gene of interest. In other instances, expression vectors are available which provide for a polylinker between a transcriptional region, also providing for the various signals associated with the processing of the messenger for translation, i.e., the cap site and the polyadenylation signal. The construction of the expression cassette comprising the regulatory regions and the structural gene may employ one or more of restriction enzymes, adapters, polylinkers, in vitro mutagenesis, primer repair, resection, or the like.

The expression cassette will usually be part of a vector which will include a marker and one or more replication systems. The marker will allow for detection and/or selection of cells into which the expression cassette and marker have been introduced. Various markers may be employed, particularly markers which provide for resistance to a toxin, particularly an antibiotic. Preferably, gentamicin resistance is employed, which provides resistance to G418 for a mammalian cell host. The replication systems may comprise a prokaryotic replication system, which will allow for cloning during the various stages of bringing together the individual components of the expression cassette. The other replication system may be used for maintenance of an episomal element in the host cell, although for the most part the replication system will be selected so as to allow for integration of the expression cassette into a chromosome of the host.

The introduction of the expression cassette into the host may employ any of the commonly employed techniques, including transformation with calcium precipitated DNA, transfection, infection, electroporation, ballistic particles, or the like. Once the host cells have been transformed, they may be amplified in an appropriate nutrient medium having a selective agent, to select for those cells which comprise the marker. Surviving cells may then be amplified and used.

Host cells which may be employed include African green monkey cell line CV1, mouse cells NIH-3T3, normal human bone marrow fibroblasts, human spleen fibroblasts, normal mouse bone marrow fibroblasts, and normal mouse spleen fibroblasts. It should be noted that in some instances, depending upon the choice of vector and cell line, the cells may become neoplastic.

Once the vector for expressing the appropriate trait has been constructed, it may be used to transform the cells by any convenient means. The cells will be allowed to grow for sufficient time to ensure that the cells are viable and are capable of producing the desired traits.

The term transforming vector or cell transformation vector as used in the present invention refers to a DNA molecule, usually a small plasmid or bacteriophage DNA capable of self-replication in a host organism, and used to introduce a fragment of foreign DNA into the host cell.

Other features of the present invention will become apparent in the course of the following descriptions of exemplary embodiments which are given for illustration of the invention and are not intended to be limiting thereof.

Exemplary Embodiments
Cell Culture

Rabbit renal proximal tubule cells were grown in primary culture by techniques reported by Humes et al. in *Lab. Invest.* 64:538–45 (1991). The cells were grown in 35 mm Corning culture dishes with serum-free, hormonally defined Dulbecco's Modified Eagle Hams F-12 media (1:1, v/v) containing L-glutamine, penicillin, streptomycin, 50 nM hydrocortisone, 5 μg/ml of insulin, and 5 μg/ml of transferrin. The cultures were maintained in a humidified 5% $CO_2$/95% air incubator at 37° C. Medium was changed every 3 to 5 days, depending on nutrient requirements based upon cell number. Cultures became confluent in 9 to 12 days. Once confluent, various agents as described below were added in 20 μl aliquots at various times to promote changes in morphologic phenotype or pattern formation.

Morphology

Specimens for ultrastructural analysis were fixed with 2% glutaraldehyde in Sorenson's buffer (pH 7.2, 310 mOsm). Postfixation occurred in 1% $OsO_4$ followed by dehydration in ethanol. Specimens were transferred through propylene oxide into monomer mixture (poly/Bed 812A, Araldite, DDSA and DMP-30) and polymerized at 60° C. Thin sections were stained with uranyl acetate and lead citrate, and examined in a Zeiss 9-S2 transmission electron microscope.

Materials

All reagents used were of the highest grade commercially available. All organic reagents were obtained from Sigma Chemical Company (St. Louis, Miss.) unless otherwise indicated. EGF (recombinant human) was obtained from Amgen Biologicals (Thousand Oaks, Calif.), TGF $β_1$ (porcine platelets) from R & D Systems (Minneapolis, Minn.). TGF-$β_1$ was dissolved in 4 mm HCl and 1 mg/ml bovine serum albumin; EGF in aqueous buffer, and RA in 95% ethanol.

Results

Simultaneous treatment of density-arrested, confluent monolayers of adult rabbit renal proximal tubule cells with TGF-$β_1$, EGF, and RA resulted in a dramatic phenotypic transformation characterized by condensed aggregates of cells in cord-like structures. Evaluation of these cellular aggregates by light and transmission electron microscopy revealed the presence of lumen formation within the interior of the cell aggregates. The lumens were bordered by tubule cells possessing a polarized epithelial phenotype with extensive microvilli formation and tight junctional complexes along the luminal border. Of note, in each aggregation of cells one or two lumen structures were usually observed in random sectioning of tissue culture preparations. The lumens and bordering polarized epithelial cells were surrounded by nonpolarized, adherent cells which did not possess tight junctional complexes.

All three factors are necessary for tubulogenesis, as demonstrated by the following experiments.

EXAMPLE 1

A density-arrested, confluent monolayer of renal proximal tubule cells in standard tissue culture was simultaneously treated with TGF-$β_1$ (10 ng/ml), EGF (1 nM), RA (0.1 μM). After 144 hours of treatment, the call culture had undergone a transformation of the monolayer into adherent cell aggregates containing an area with a well defined lumen, as seen by light microscopy (magnification ×400). Utilizing transmission microscopy, the lumen could be seen to be bordered by tubule cells possessing a polarized epithelial cell phenotype with well-developed epithelial microvilli (magnification ×6500). Further magnification (×19900) with electron microscopy demonstrated that tight junctional complexes existed between the cells bordering the lumen near the apical surface.

COMPARATIVE EXAMPLE 2

Addition of TGF-$β_1$ (10 ng/ml) to a density-arrested, confluent monolayer of renal proximal tubule cells resulted in a phenotypic transformation of the monolayer to form solid aggregates of adherent cells as observed by light microscopy (magnification ×400). Cells lining the surface of the cell aggregates possessed occasional broad based microvilli and tight junctional complexes, but no lumen formation was observed.

COMPARATIVE EXAMPLE 3

Simultaneous treatment of a confluent monolayer with TGF-$β_1$ (10 ng/ml) and EGF (1 nM) produced a similar morphologic transformation into cell aggregates which were, in general, larger than those seen with TGF-$β_1$, due to greater number of adherent cells within the condensed aggregate, as observed by light microscopy (magnification ×400). However, no lumen formation or polarized epithelial phenotype was found.

COMPARATIVE EXAMPLE 4

The simultaneous exposure of the epithelial monolayer to TGF-$β_1$ (10 ng/ml) and RA (0.1 μM) promoted intracytoplasmic vacuolization as observed by light microscopy (magnification ×400). However, these areas never developed into lumens with polarized epithelial phenotype, in contrast to the experiment with TGF-$β_1$, RA and EGF, administered in combination.

COMPARATIVE EXAMPLE 5

Treatment of the monolayer with RA alone (0.1 μm) or RA (0.1 μm) and EGF (1 nM) had no dramatic effect on the appearance of the monolayer.

These results indicate that transforming growth factor-$β_1$, epidermal growth factor, and all-trans retinoic acid play important roles in tubulogenesis.

EXAMPLE 2

Isolation of renal stem cells from adult mammalian kidneys

Lining epithelia of various organs of the adult mammal, such as the gastrointestinal tract and the skin, are characterized by rapid and continuous cell turnover. The finite lifespan of the terminally differentiated epithelial cell necessitates replacement through proliferation of a subpopulation of cells, usually referred to as stem cells, with a high capacity for replication and an ability to produce differentiated progeny (Garlick et al., *J. Invest. Dermatol.* 97(5): 824–829, 1991; Hall et al., *Development* 106:619–633, 1989; and Potten et al. *Development* 110:1001–1020, 1990). The adult kidney tubule is another lining epithelium but, in contrast to the intestinal and epidermal epithelia, is a much slower self renewing cell layer with a replacement rate of only one tubule cell per nephron per day (Prescott et al. *Clin. Sci.* 31:425–435, 1966). Following severe ischemic or toxic injury, however, the adult renal proximal tubule epithelium demonstrates tremendous capacity for rapid self-renewal (4,10,34). This regenerative capacity results in the kidney to recover normal function within days following ischemic or toxic injury of a magnitude severe enough to produce complete organ failure. The ability of the kidney to recover full function after such severe injury is also due to the ability of the regenerating lining proximal tubule epithelium to both differentiate and pattern form into correct morphologic structure in order to function as a transporting epithelium with appropriate spatial and vectorial components.

Cell Culture

Adult rabbit renal proximal tubule cells were grown in primary culture by techniques previously reported by this laboratory (11, 12). The cells were grown in 35 mm Corning culture dishes with serum free hormonally defined Dulbecco's modified Eagle (DME) Ham's F012 media (1:1, v/v) containing L-glutamine, penicillin/streptomycin, hydrocortisone, insulin, transferrin. Once confluent, cultures were processed for passage. Cultures were treated with 1.0 $\mu$M all-trans-retinoic acid (Sigma) and 10 nM recombinant human epidermal growth factor (Amgen) for 24 hours prior to passage. Cell plates were treated with trypsin for 4 minutes at 37° C. followed by 0.1% soybean trypsin inhibitor. The cells were then removed and pelleted by centrifugation at which time various amounts of media were added to make the appropriate dilution of cells. Once passed, the cells were grown in media containing epidermal growth factor (EGF) and retinoic acid (RA) until confluency. In this manner, cells could be harvested at any time after passage for either dispersement and suspension into three-dimensional collagen gels or for continual passage of cells.

Suspension of Cells in Collagen

Collagen (Vitrogen 100, Celltrix Labs) was mixed with 10× phosphate buffered saline and pH adjusted to 7.4. Cells ($5 \times 10^5$ were suspended in 250 ul of media and uniformly dispersed in 750 ul of collagen prior to gelation. An aliquot of the resulting mixture (250 ul) was placed into a chilled Anocell-10 cell culture insert and allowed to set at 37° without $CO_2$ for 45–60 minutes. After gelation, the appropriate culture media was added and the cells were cultured for 7–21 days. Best results occurred with the use of 1.8 mg of collagen/ml.

Recombinant Retrovirus

A high titer, replication defective retrovirus was constructed to encode for the *E. coli* lac Z gene ($\beta$-galactosidase), thereby providing a convenient assay for the provirus for lineage analysis. The recombinant retroviral vector (a generous gift from Dr. James Wilson, University of Pennsylvania) was derived from a wild-type Moloney provirus similar to MFG in which the human growth hormone cDNA was replaced with lac-Z cDNA (6). Briefly, the retroviral vector p-mLac Z was transfected into the ecotropic retroviral packaging cell line $\psi$-cre (5,18). Twenty-five clones were isolated and screened for production of p-mlacZ virus by detecting $\beta$-galactosidase activity with the chromogenic substrate 5-bromo-4-chloro-3-undolyl-$\beta$-D-galactoside (X-gal) stain; the highest virus-producing cell line was identified and used to cross infect the amphotropic cell line $\psi$-crip. Clones producing amphotropic virus were isolated, and the highest titer clone was selected (AZ-5). The AZ-5 virus has a titer of $10^6$ colony forming units (CFUs)/mL, and is free of replication competent virus as determined by a sensitive provirus rescue assay (16,33). To harvest virus, the AZ-5 cells were seeded into 10 cm plates ($5 \times 10^5$ cells per plate) in DMEM containing 10% fetal calf serum and penicillin/streptomycin. Twenty-four hours after seeding the media was changed, and after an additional 24 hours the virus containing supernatant was harvested and filtered through a 0.45 u filter. Renal proximal tubule cells were prepared after growth in primary culture and 2 or 3 serial passages. Under subconfluent conditions, renal tubule cells were exposed to undiluted or diluted stocks of recombinant retrovirus for 24 hours in the presence of Polybrene (8 ug/ml). After transduction the culture medium was then removed and replaced with serum-free, hormonally defined culture medium supplemented with RA and EGF. Cells were then grown to confluence, removed from culture plates and suspended into collagen gels for 10–14 days.

Histologic Processing

Collagen gel cultures were fixed in situ with 2% glutaraldehyde and Sorenson's buffer (pH 7.2, 310 mOsm). Semithin and thin sections were prepared with standard techniques reported for this laboratory (13,14). Thin sections were examined with a Zeiss 9-S2 electron microscope. To process Collagen gels for X-gal staining, gels were fixed in 0.5% glutaraldehyde for 2 hours, washed twice with PBS containing 1 mM $MgCl_2$, and incubated with a solution containing 1 mg/ml X-gal in PBS for 24 hours at 37° C. Gels were then rinsed twice with PBS for 10 minutes, followed by addition of 2% glutaraldehyde for 24 hours. Gels were embedded in paraffin, sectioned and processed for light microscopy. Each processed collagen gel was quantitatively analyzed by examining serial sections (4–6 um) of each tubule cluster to determine whether it was composed of all X-gal positive cells. The tubules were comprised of approximately 40–150 cells. X-gal staining was easily detected to the level of individual cells.

RESULTS

In an attempt to growth select for renal proximal tubule cells possessing the ability to serially replicate but retain the capability for differentiated morphogenesis, retinoic acid (RA) and epidermal growth factor (EGF) were chosen for three reasons. First, previous work with skin keritinocytes in tissue culture suggested that cells with stem cell-like characteristics were enriched in cell culture when growth in conditions which induced premature terminal differentiation (23,24). Second, RA has been demonstrated to be an effective differentiating agent in embryonal stem cells and in renal proximal tubule cells in tissue culture (13,28). Third EGF is the most potent renal proximal tubule cell mitogen presently described (14,22). Thus, the combination of a potent growth promoter, EGF, and a differentiating agent, RA, would provide positive selection pressure for cells which have a high capacity for replication and negative selection pressure for cells which are terminally differentiating. Although serial passage of renal proximal tubule cells have been difficult to achieve previously, these growth conditions with RA and EGF have resulted in an ability to grow these cells for more than 20 serial passages. The use of both RA and EGF were necessary for consistent passage of these cells.

Figure 1B:
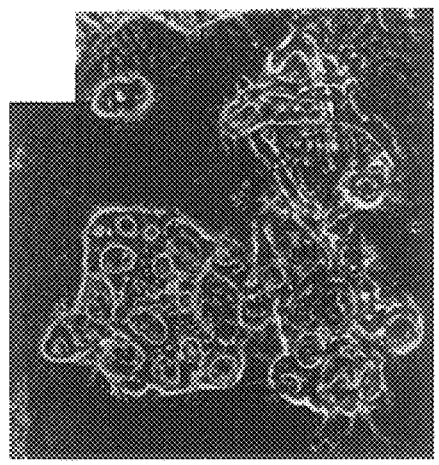
Figure 1C:
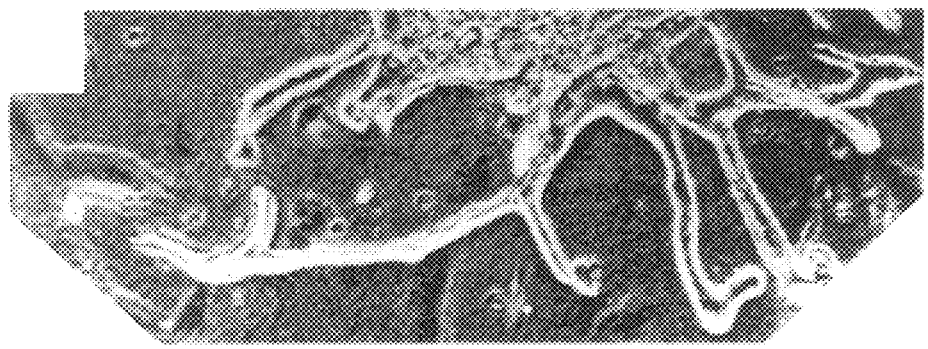
Figure 2A:
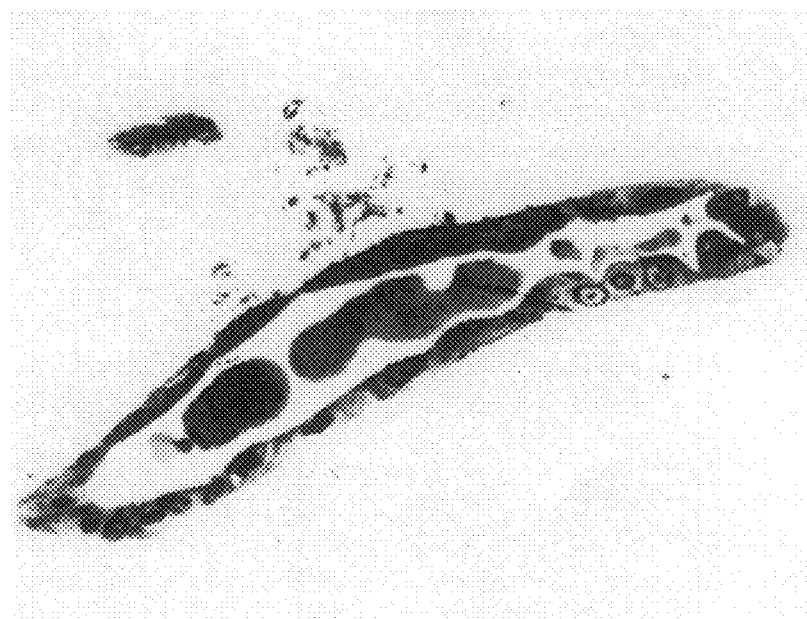
FIGS. 2a–2f is a photograph showing a representative morphology of an adult renal proximal tubule cells in tissue culture. After 1 serial passage, renal tubule cells were dispersed and suspended in three-dimensional collagen gels and cultured for 7–14 days. Semithin sections of the collagen preparation demonstrated that these cells formed tubular structures; thin sections revealed that the centralized lumens were bordered by well-polarized cells with apical microvilli and tight junctional complexes. (a) Semi-thin section of renal proximal tubule cells cultured for 14 days and forming a tubular structure in a cylindrical array when sectioned longitudinally (500×). (b) Semi-thin section of renal proximal tubule cells cultured for 14 days and forming a tubular structure in cross section (500×). (c) Thin section of renal tubule cell aggregate initiating lumen formation after culture for 7 days (3,300×). (d) Thin section (of FIG. 1c at higher power) demonstrating renal tubule cell aggregate composed of polarized cells along the developing lumen. The apical surface of these cells is rich in microvilli and contains multiple tight junctional complexes (14,400×). (e) Thin section of a mature tubule structure in cross section with a centralized lumen after 14 days in culture (3,300×). (f) Thin section across the wall of a mature renal tubule in culture for 14 days. The renal tubule cells possess a well differentiated polarized proximal tubule cell phenotype within a smooth basal structure in contact with the collagen matrix and a luminal surface possessing apical microvilli and a tight juntional complex (arrowhead) between cells bordering the lumen (denoted by *) near the apical surface (15,000×).
Figure 2B:
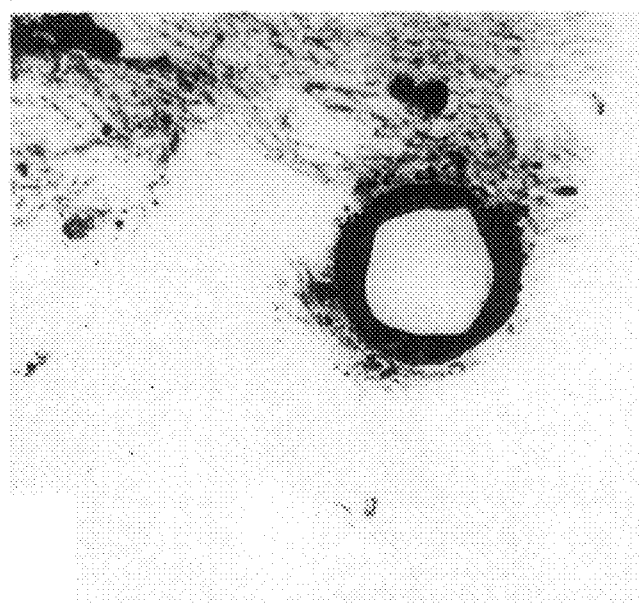
Figure 2C:
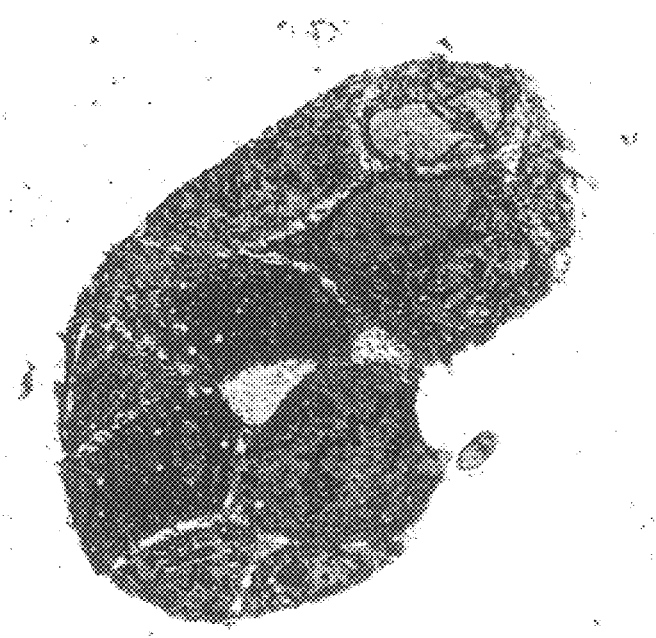
Figure 2D:
Figure 2E:
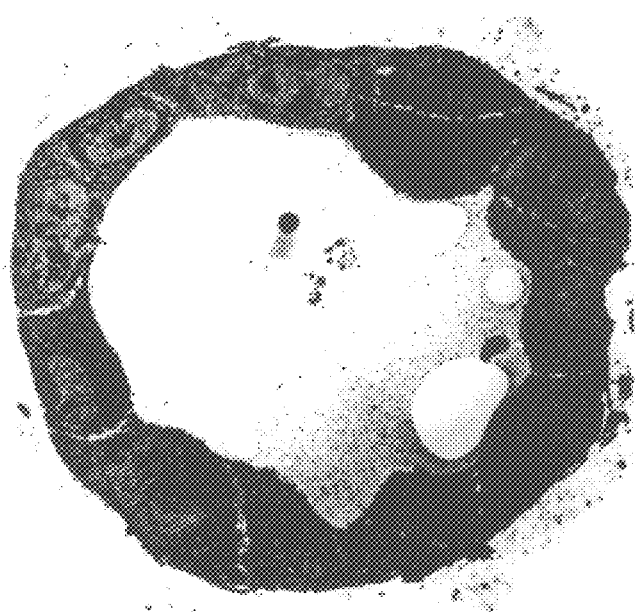
Figure 2F:
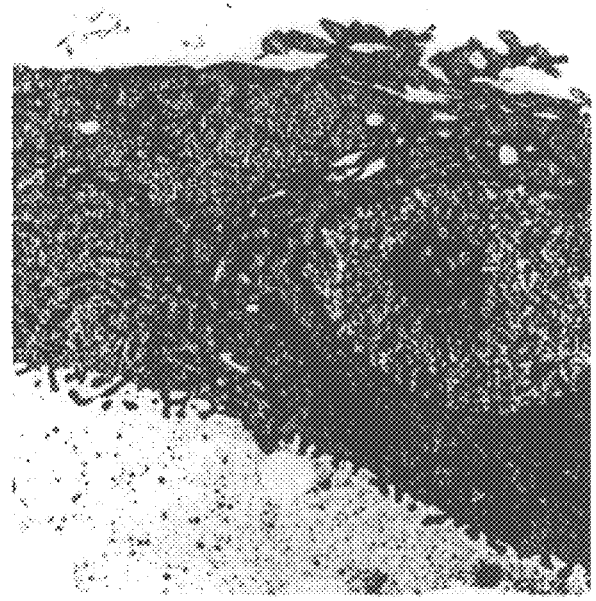
Figure 3A:
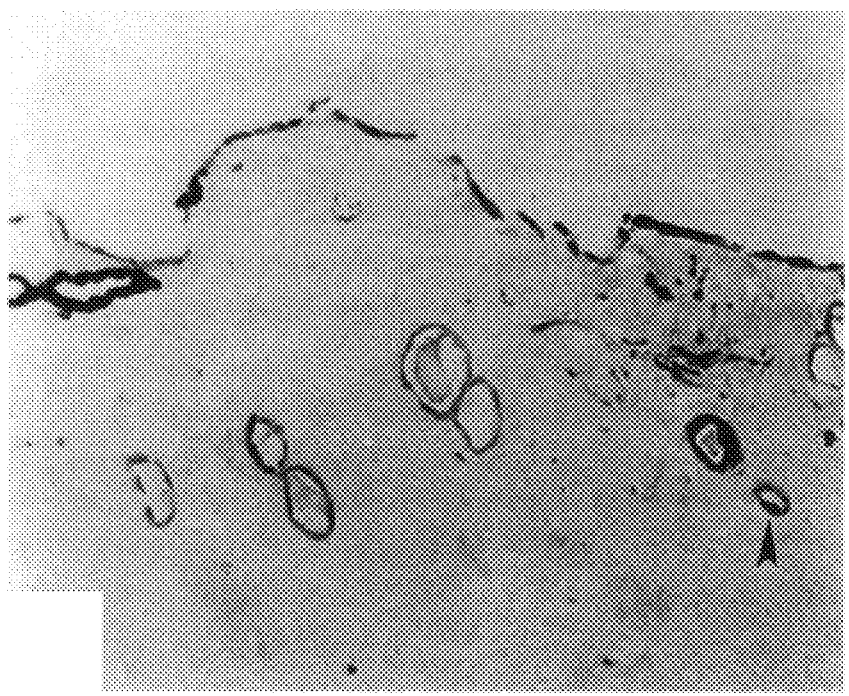
FIGS. 3a–3d is a photograph showing a representative histochemical staining for X-gal in sections of collagen gels containing renal proximal tubule cells in tissue culture. Cells were exposed to an undiluted stock solution of a replication incompetent, amphotrophic retrovirus containing the lac-Z gene, suspended in three-dimensional collagen gels and grown for 14 days. A. X-gal stained collagen gel showing clones of labeled cells derived from transduced progenitors. Positively stained cells were found in the monolayer covering the surface of the gel and in tubular structures within the gel. Tubules were composed of all X-gal negative, all X-gal positive, or mixture of X-gal negative and X-gal positive cells (arrowhead). Light micrograph (125×). B. Light micrograph (250×) using Nomarski optics of X-gal stained collagen gel displaying tubules within the gel in cross-section and longitudinal section composed of all X-gal positive cells. C. Light micrograph (250×) using Nomarski optics of X-gal stained gel containing tubules composed of all X-gal positive or all X-gal negative cells. D. Higher power light micrograph (400X) of field in panel C demonstrating the X-gal staining restricted to the cell cytoplasm, so that the cell nuclei are unstained.
Figure 3B:
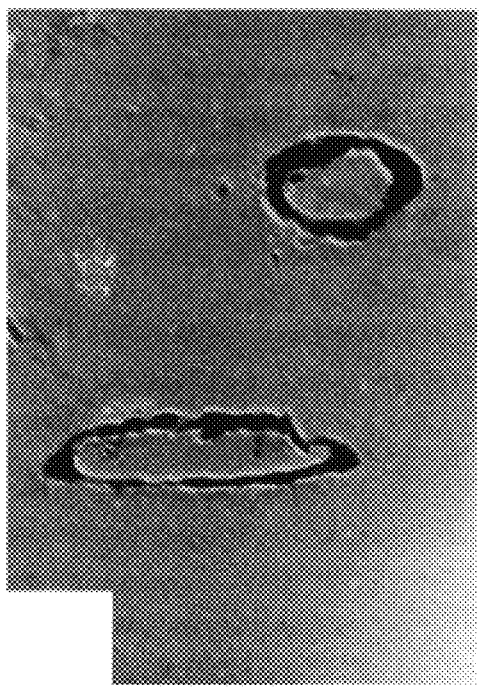
Figure 3C:
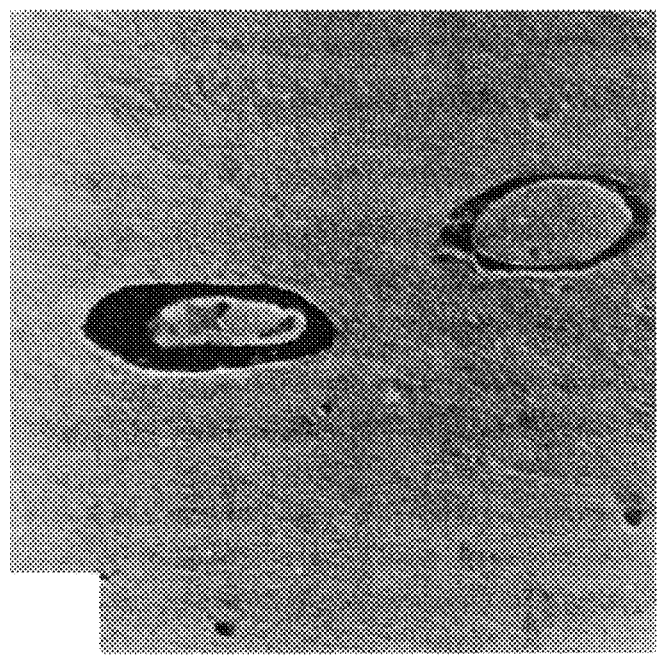
Figure 3D:
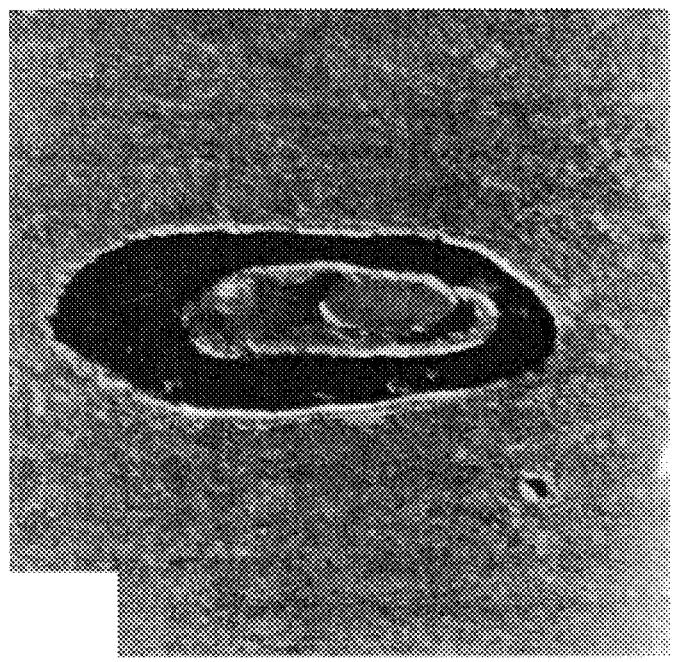

To test the ability of these renal tubule cells to morphologically differentiated and pattern form into tubule-like structures, adult rabbit renal proximal tubule cells were grown in primary culture followed by growth under selection pressure with RA and EGF for several passages. Renal tubule cells grown under this selection condition were then dispersed to prepare a single cell preparation, suspended in three-dimensional collagen gels and grown in serum-free, hormonally defined culture media supplemented with RA and EGF for 7 to 14 days (1,19,35). Within several days, cells grown under these conditions in collagen gels were observed to form luminal tubular structures by phase contrast microscopy (FIGS. 1A–1C). In fact, progressive passage of cells promoted increasingly more defined tubular structures. Semithin sections of the collagen preparation confirmed the tubular nature of the cell clusters. As seen in FIGS. 2A and 2B, cell aggregates within the collagen gel formed monolayers of cells in cylindrical arrays surrounding centralized lumens. Thin sections demonstrated that the lumens were bordered by polarized epithelial cells with well defined microvilli and tight junctional complexes along the apical luminal border (FIGS. 2C–2F). Of note, under these conditions a monolayer of cells also grew along the surface of the collagen gel. These surface cells possessed broad based microvilli projecting into the culture medium along the apical border. Tight junctional complexes were also present between these surface cells near the apical border exposed to the culture medium. If EGF or RA alone or in combination were omitted from the culture media, tubule-like structures within the collagen gel did not form.

These initial experiments were able to define growth conditions for renal proximal tubule cells to pattern form into tubules with a differentiated, polarized epithelial cell phenotype in vitro. It was unclear, however, whether these tubules were derived from aggregation of multiple cells with a limited capacity for replication or derived from clonal expansion of a single progenitor. Recent reports have documented that replication defective, recombinant retroviruses have been successfully employed to genetically mark progenitor cells to investigate cell lineage in embryonic development in vivo and tissue culture in vitro (2,9,27,29,32). After transduction of a cell, the integrated retroviral genome, now called the provirus, is inherited without dilution to all the progeny of the transduced cell and can be used as a lineage marker. Construction of a high titer, replication defective recombinant retrovirus which encodes for the *E. coli* lac Z gene (β-galactosidase) provides for a convenient assay for the provirus with a simple histochemical stain for β-galactosidase (2,9,27,29,32).

An amphotropic recombinant retrovirus which encodes for β-galactosidase was used for cell lineage analysis of renal tubule cells in tissue culture (5,16,18,33). Renal proximal tubule cells were grown in primary culture and serially passed. After 2 or 3 passages, tubule cells were transduced with the recombinant retrovirus and transferred into three dimensional collagen gels. After 10–14 days of growth, cells in the collagen gel were processed for detection of β-galactosidase activity with the chromogenic substrate 5-bromo-4-chloro-3-indolyl-↓-D-galactoside (X-gal) which forms a dark blue precipitate in transduced cells and their progeny. Labeled cells were found throughout the collagen gel in histologic sections. X-gal positive cells were found along the monolayer of tubule cells lining the surface of the collagen gel and in tubule structures (FIG. 3). Serial sections of collagen preparations demonstrated that most tubules were devoid of X-gal positive cells but occasional tubules were comprised of all labeled cells or contained a mixture of both X-gal positive and X-gal negative cells. On serial sections, some tubules contained as many as 150 cells, all of which were positively stained for X-gal. Of note, mock infected cells suspended and grown in collagen gels did not display background β-galactosidase activity.

To determine whether tubules arose from clonal expansion of a single genetically tagged progenitor or aggregation of multiple tagged cells, renal tubule cells were transduced with serial dilutions of the recombinant retrovirus. Serial sections of collagen gels, processed for X-gal straining, demonstrated that tubules composed of all X-gal positive cells still developed with increasing dilutions of viral stock, but developed with decreasing frequency. The observation that the number of X-gal positive cells within homogeneously stained tubules remained the same while the number of homogeneously stained aggregates decreased with virus dilution suggested that in vitro tubulogenesis occurred from clonal expansion of a single genetically tagged cell rather than from aggregation of multiple tagged cells.

Figure 4:
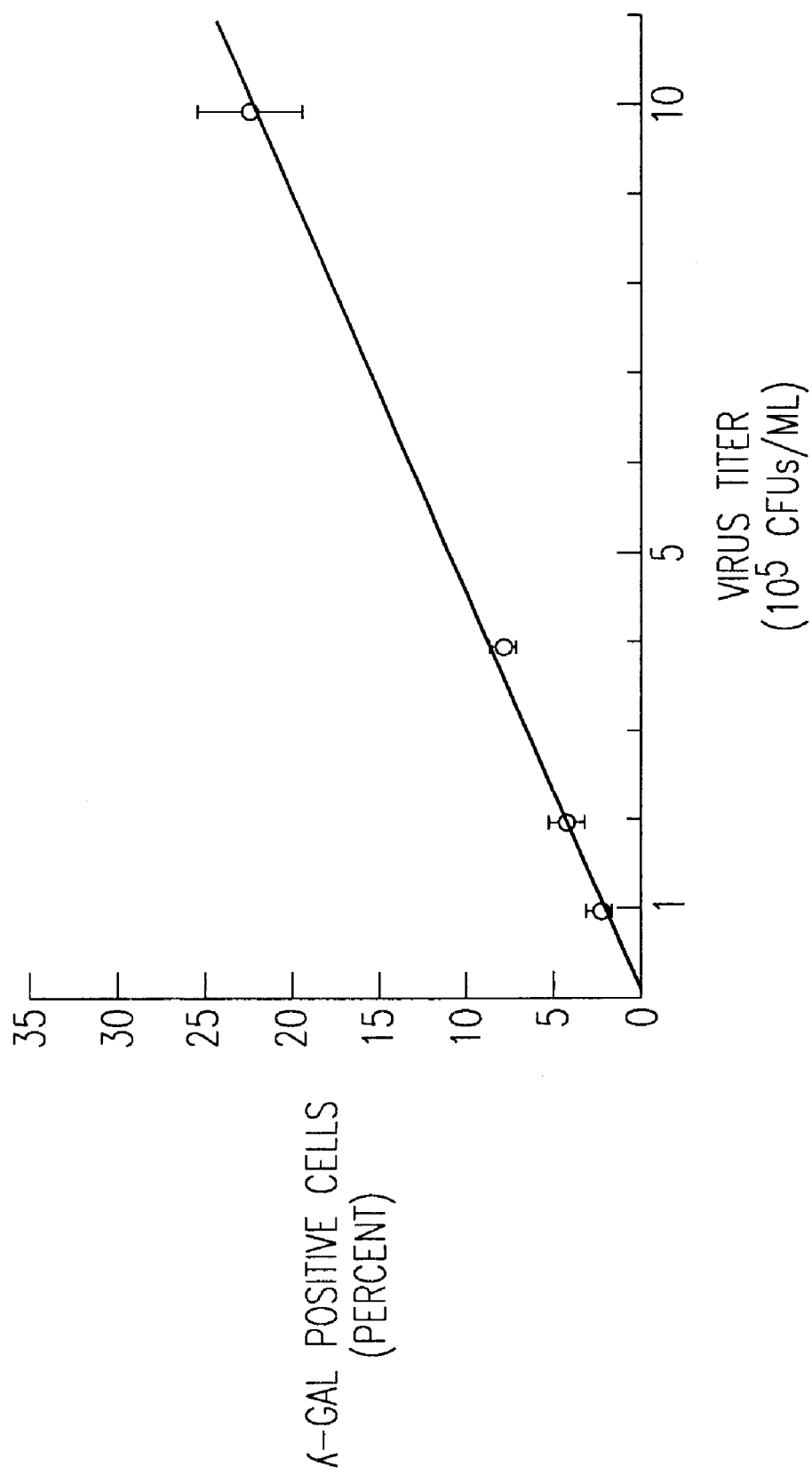
FIG. 4 is a graph of the percentage of X-gal positive cells in the surface monolayer of collagen gels grown in tissue culture for 14 days plotted against various transducing dilutions of recombinant retrovirus. Solid line represents linear regression analysis for the plotted points.

To define the statistical probability that tubulogenesis in vitro arose from clonal expansion of a single cell, serial sections of 16 collagen gels utilizing 4 separate primary cultures and 4 viral dilutions were evaluated. The transduction efficiency of renal tubule cells at the selected dilutions of recombinant retrovirus was calculated by determining the percentage of X-gal positive and X-gal negative ells in the monolayer along the surface of the gel. As shown in FIG. 4, the percentage of total cells which were X-gal positive after 14 days of growth in culture had an observed linear relationship to the dilution of virus, demonstrating that the number of genetically tagged cells was directly proportional to the amount of virus exposed to the cells. Using the observed frequency of X-gal positive cells in the monolayer, the expected frequency of homogeneously stained tubules arising from the random aggregation of two independently transduced cells was calculated. The exact probability comparing the expected and observed frequencies was then determined for each viral dilution. As displayed in Table 1, the probabilities that homogeneously stained tubules arise from two transduced cells were highly unlikely for all viral dilutions with the lowest probability being vanishingly small at $4.8 \times 10^{-5}$ for the most dilute viral stock.

TABLE 1

DILUTION ANALYSIS OF CELL LINEAGE IN KIDNEY TUBULES

| VIRUS DILUTION | PERCENT X-GAL POSITIVE CELLS IN MONOLAYER | PERCENT TUBULES WITH ALL X-GAL POSITIVE CELLS | | PROBABILITY |
|---|---|---|---|---|
| | | EXPECTED | OBSERVED | |
| 1 | 22.0 ± 2.9 | 5.51 ± 1.33 | 18.12 ± 1.58 | $2.2 \times 10^{-4}$ |
| 2.5 | 7.9 ± 0.1 | 0.62 ± 0.02 | 8.66 ± 2.91 | $1.0 \times 10^{-2}$ |
| 5 | 3.8 ± 0.9 | 0.17 ± 0.07 | 6.55 ± 3.20 | $4.8 \times 10^{-10}$ |

Data presented as mean ± SE for n = 3–9 collagen gels prepared from passed cells derived from 4 separate primary cultures. Exact probability was determined by the use of cumulative binomial distribution analysis.

The probability for a totally X-gal positive tubule arising from the aggregation of more than two transduced cells would be even smaller. This analysis strongly suggests that kidney tubulogenesis in collagen gels arise from the clonal expansion of single progenitor cells rather than from aggregation of two or more cells.

1. Bennett, D. C., *Nature* 285:657–659, 1980.
2. Bunge et al., *Science* 243:229–231, 1989).
3. Cieslinski et al., *J. Am. Soc. Neph.* 3:465, 1992).
4. Cuppage et al., *Lab. Invest.* 21:449–459, 1969.
5. Danos et al., *Proc. Natl. Acad. Sci. USA* 85:6460–6464, 1988.
6. Dhawan et al., *Science* 254:1509–1512, 1992.
7. Garlick et al., *J. Invest. Dermatol.* 97(5):824–829, 1991.
8. Hall et al., *Development* 106:619–633, 1989.
9. Herzlinger et al., *Development* 114:565–572, 1992.
10. Humes et al., *J. Clin. Invest.* 84:1757–1761, 1989.
11. Humes et al., *Renal. Phys. Biochem.* 14:253–258, 1991.
12. Humes et al., *Am. J. Phys.* 262:F540–F545, 1992.
13. Humes et al., *Exp. Cell. Res.* 201:8–15, 1992.
14. Humes et al., *Lab. Invest.* 64:538–545, 1991.
15. Humes et al., *Kidney Int.* 43:575–584, 1993.
16. Krauss et al., *Human Gene Ther.* 2:221–228, 1991.
17. Liu et al., *J. Am. Soc. Neph.* 3:472, 1992.
18. Mann et al., *Cell* 33:153–159, 1983.
19. Montesano et al., *Cell* 42:469–477, 1985.
20. Montesano et al., *Cell* 67:901–908, 1991.
21. Nakamura et al., *Kidney Int.* 41:1213–1221, 1992.
22. Norman et al., *Am. J. Physiol.* 253:F299–F309, 1987.
23. Parkinson et al., *Carcinogenesis* 3:525–531, 1982.
24. Parkinson et al., *Carcinogenesis* 4:857–861, 1983.
25. Potten et al. *Development* 110:1001–1020, 1990.
26. Prescott et al. *Clin. Sci.* 31:425–435, 1966.
27. Price et al. *Proc. Natl. Acad. Sci. USA* 84:156–160, 1987.
28. Rogers et al. *J. Cell Biol.* 110:1767–1777, 1990.
29. Sanes et al. *EMBO J.* 5:3133–3142, 1986.
30. Santos et al. *Dev. Biol.* 163:525–529, 1994.
31. Taub et al. *Proc. Natl. Acad. Sci. USA* 87:4002–4006, 1990.
32. Turner et al. *Nature* 328:131–136, 1987.
33. Wilson et al. *Science* 248:1413–1416, 1990.
34. Witzgall et al. *J. Clin. Invest.* 93:2175–2188, 1994.
35. Yang et al. *Proc. Natl. Acad. Sci. USA* 76:3401–3405, 1979.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An isolated and purified population of renal stem cells which has been cultured and expanded ex vivo, wherein the cells have been passaged at least three times, wherein the population retains renal stem cells after at least three passages, and wherein the stem cells are capable of differentiating into renal proximal tubule cells.

2. The population of claim 1, which also contains renal proximal tubule cells, wherein some of the renal proximal tubule cells have undergone kidney tubulogenesis.

3. The population of claim 1, wherein the renal stem cells are transformed with DNA encoding a polypeptide.

* * * * *

UNITED STATES PATENT AND TRADEMARK OFFICE
CERTIFICATE OF CORRECTION

PATENT NO. : 6,410,320 B1
DATED : June 25, 2002
INVENTOR(S) : H. David Humes

It is certified that error appears in the above-identified patent and that said Letters Patent is hereby corrected as shown below:

Column 2,
Line 12, "has not-been" should read -- has not been --;
Line 35, "Dziadpk" should read -- Dziadek --.

Column 5,
Line 13, "*Accad.*" should read -- *Acad* --.

Column 6,
Line 7, "man employ" should read -- may employ --.

Column 8,
Line 11, "the call" should read -- the cell --.

Column 12,
Line 19, "straining" should read -- staining --;
Line 35, "ells in the" should read -- cells in the --.

Column 13,
Line 8, "1989)." should read -- 1989. --;
Line 9, "1992)." should read -- 1992. --.

Signed and Sealed this

Twenty-fifth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,410,320 B1  Page 1 of 1
DATED : June 25, 2002
INVENTOR(S) : H. David Humes It is certified that error appears in the above-identified patent and that said Letters Patent is hereby corrected as shown below:

Title page,
Item [63], Related U.S. Application Data, "[63] Continuation-in-part of application No. 07/844,758, filed on March 2, 1992, now Pat. No. 5,429,938." should read
-- [63] Continuation of 08/449,912, filed on May 25, 1995, which is a Continuation-in-part of application No. 07/844,758, filed on March 2, 1992, now Pat. No. 5,429,938. --

Signed and Sealed this

Third Day of May, 2005

JON W. DUDAS
*Director of the United States Patent and Trademark Office*